US00PP09597P

United States Patent [19]

Skotak, Jr.

[11] Patent Number: Plant 9,597

[45] Date of Patent: Jul. 2, 1996

[54] NEOREGELIA PLANT NAMED 'ULTIMA'

[75] Inventor: Chester Skotak, Jr., Alajuela, Costa Rica

[73] Assignee: Dura Flor S.A., Alajuela, Costa Rica

[21] Appl. No.: 422,531

[22] Filed: Apr. 14, 1995

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Foley & Lardner

[57] ABSTRACT

A new and distinct Neoregelia named 'Ultima,' characterized by leaves that have a greenish-white center bordered by variegation down the entire length of the leaf and dark green margins, finely serrated leaf margins, uniformly rosette plant form with long, lingulate and recurved leaves that are bright red at the base in the center of the plant at flowering.

3 Drawing Sheets

The present invention comprises a new and distinctive cultivar of Neoregelia hybrid, hereinafter referred to by the cultivar name 'Ultima.' Neoregelia species are tank epiphytes with stemless inflorescences and flowers that barely rise above the water in the center of plants. 'Ultima' can be advantageously grown as a single pot plant in order to display its symmetrically rosette plant form.

The new cultivar is a product of a planned breeding program, and was originated from a cross made during such a program is Balsa, Costa Rica in 1990. The female, or seed parent was *Neoregelia carolinae*× *Neoregelia concentrica 'D.'*. The male, or pollen parent was *Neoregelia McWilliamsii*× *Neoregelia compacta.*

'Ultima' was discovered and selected as a flowering plant within the progeny of the stated cross by Chester Skotak, Jr. in 1992 in a controlled environment in Balsa, Costa Rica. Subsequent asexual reproduction by removal of offsets has demonstrated that the combination of characteristics as herein disclosed for the new cultivar are firmly fixed and are retained through successive generations of asexual reproduction.

The new cultivar has not been observed under all possible environmental conditions. The phenotype may vary with variations in environment such as temperature, light, intensity and day length, without any variation in the genotype of the plant.

The following traits have been repeatedly observed and are determined to be basic characteristics of 'Ultima' that in combination distinguish this Neoregelia as a new and distinct cultivar:

1. The center of each leaf is greenish-white (RHS 145 C-D) bordered by variegation down the entire length of the leaf and a dark green margin (RHS 137 A- B).

2. The basal portion of the innermost leaves is bright red (RHS 57A) and this red color overlays the green and white portions of the leaves.

3. The margins of the leaves are finely serrated.

4. The form of the plant is a uniform rosette with long, lingulate and recurved leaves.

The following observations, measurements and values describe plants grown in Balsa, Costa Rica and Goulds, Fla., U.S.A. under greenhouse conditions which closely approximate those generally used in horticultural practice. Color references are made to The Royal Horticultural Society (R.H.S.) Colour Chart, except where general color terms of ordinary significance are used. The color values were determined at approximately 10:00 a.m. on Apr. 12, 1995 under natural light in Washington, D.C., U.S.A.

The new cultivar can be compared to *Neoregelia McWilliamsii.* 'Ultima' has variegation in the center of the leaf while *N. McWilliamsii* does not. Unlike *N. McWilliamsii*, 'Ultima' has finely serrated leaf margins.

The accompanying photographic drawings show typical characteristics of the new cultivar with colors being as true as possible with illustrations of this type.

Sheet 1 is a side view of the plant.

Sheet 2 is a top view of the plant.

Sheet 3 is a closeup of the plant center, showing an open flower.

Classification:

*Botanical.*—Neoregelia hybrid, cv. 'Ultima'.

*Commercial.*—Neoregelia 'Ultima'.

Parentage:

*Male parent.*—*Neoregalia McWilliamsii.*

*Female parent.*—*Neoregalia carolinae* × *Neoregalia concentricia 'D.'*

Propagation: Vegetatively by removal of offsets.

Plant description: From 26 cm. to 30 cm. tall when grown in 12.5 cm. pots, and approximately 60 cm. in diameter when fully grown.

*Growth habit.*—Low spreading rosette.

Leaves:

*Form.*—Blades long, lingulate, recurved, broadly rounded and apiculate.

*Size.*—Length: 32 cm. to 40 cm. Width: 2.5 cm tip – 4 cm middle.

*Texture.*—Smooth upper and lower surface and finely serrated leaf margins.

*Veins or ribs.*—None.

*Color (RHS).*—Upper surface: The center of each leaf is greenish white (RHS 145 C-D) bordered by variegation down the entire length of the leaf and a dark green margin (RHS 37 A-B). The basal portion of the innermost leaves is bright red (RHS 57A) and this red color overlays the green and white portions of the leaves. Lower surface: Same as upper surface.

*Number of leaves.*—30 plus.

Flowers:

*Arrangement.*—Inflorescence is a deeply sunken rosette simple and many-flowered.

*Color.*—Petals with a dark blue apex (RHS 110 A- B) with white center.

*Fruit.*—Ovary ellipsoid and approximately 10 mm long with a pink color.

*Duration of flowers.*—Individually only 1 day — as a whole 1 month.

*Other significant characteristics.*—The basal portion of innermost leaves maintains its red color for up to 3 months.

Reproductive organs:

*Stamens.*—Pale yellow. Anther: White.

Pistils.—Ovary: Ellipsoid and approximately 10 mm long with 5 mm diameter.

Resistance to disease: Resistance to Fusarium sp. and several other pathogenic fungi found in Costa Rica.

General observations: Plants grow vigorously.

I claim:

1. A new and distinct cultivar of Neoregelia plant named 'Ultima,' as illustrated and described.

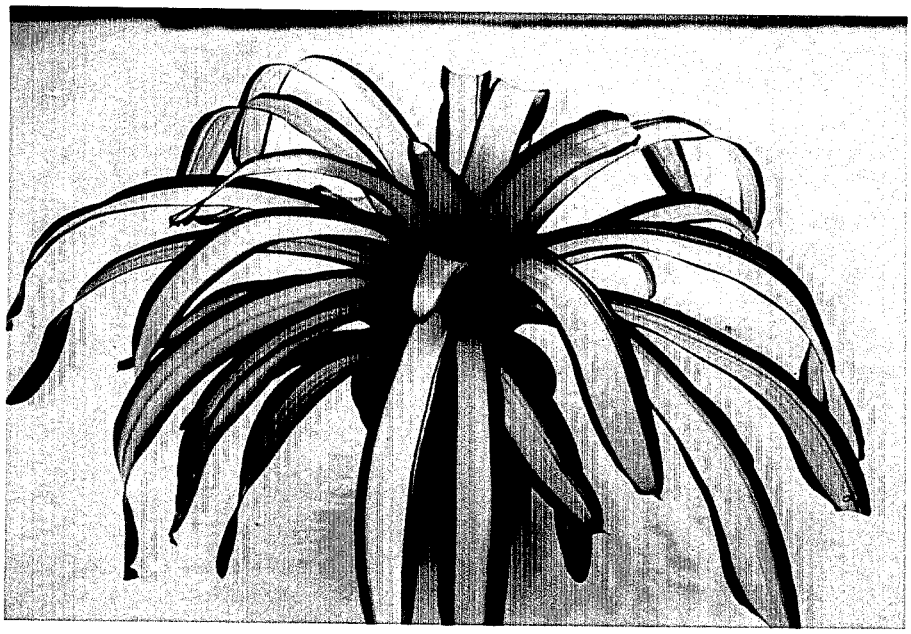

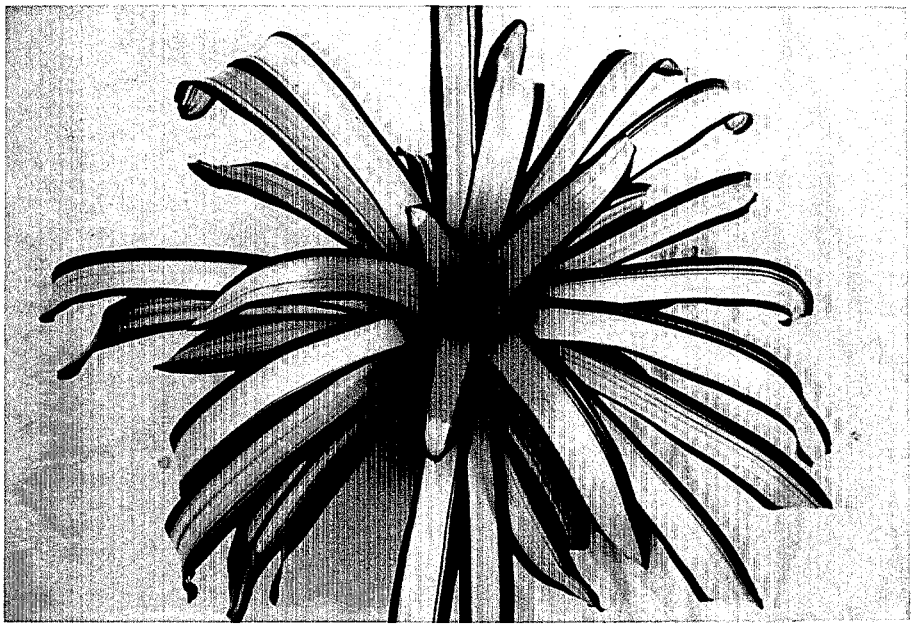

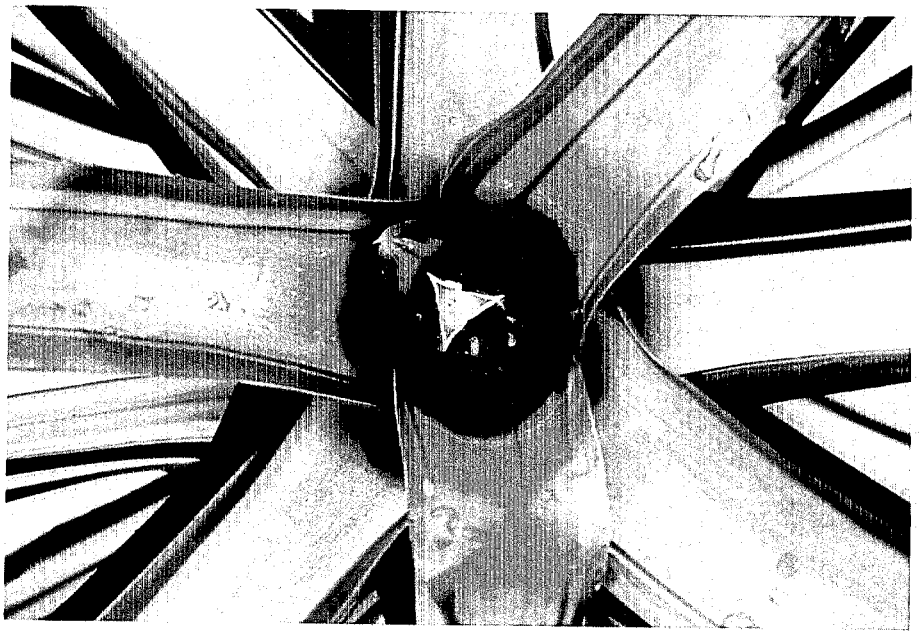

* * * * *